US012788462B2

(12) United States Patent
Dugan et al.

(10) Patent No.: US 12,788,462 B2
(45) Date of Patent: Nov. 10, 2026

(54) RESORBABLE SELF TAPPING SCREW

(71) Applicant: Stryker European Operations Limited, Carrigtwohill (IE)

(72) Inventors: Brendan Dugan, Bedminster, NJ (US); Donal O'Mahony, Clare (IE); Brittany Fuchs, Centerport, NY (US); Noelle Maguire, Limerick (IE); Aisling McDermott, Limerick (IE)

(73) Assignee: Stryker European Operations Limited, Carrigtwohill (IE)

( * ) Notice: Subject to any disclaimer, the term of this patent is extended or adjusted under 35 U.S.C. 154(b) by 298 days.

(21) Appl. No.: 18/125,948

(22) Filed: Mar. 24, 2023

(65) Prior Publication Data

US 2024/0315745 A1 Sep. 26, 2024

(51) Int. Cl.
*A61B 17/86* (2006.01)
*A61B 17/00* (2006.01)

(52) U.S. Cl.
CPC ........ *A61B 17/863* (2013.01); *A61B 17/8635* (2013.01); *A61B 2017/00004* (2013.01)

(58) Field of Classification Search
CPC ...... A61B 2090/037; A61B 2017/8655; A61B 17/863; A61B 17/8635; A61B 2017/044; A61B 2017/042; F16B 13/061; F16B 13/0808; F16B 13/002
See application file for complete search history.

(56) References Cited

U.S. PATENT DOCUMENTS 3,143,916 A * 8/1964 Rice ...................... F16B 37/065 411/37
4,760,843 A * 8/1988 Fischer ................ A61B 17/686 606/313
5,084,050 A 1/1992 Draenert
5,209,753 A * 5/1993 Biedermann ...... A61B 17/8685 606/314
5,336,240 A 8/1994 Metzler et al.
5,489,210 A * 2/1996 Hanosh ................ A61C 8/0033 433/173
5,496,326 A 3/1996 Johnson
(Continued)

FOREIGN PATENT DOCUMENTS

AU 2017362872 A1 5/2019
EP 1302170 A2 4/2003
(Continued)

OTHER PUBLICATIONS

Extended European Search Report including Search Opinion from EP Appl. No. 24165537.2, dated Jul. 23, 2024, pp. 1-8.
(Continued)

*Primary Examiner* — David W Bates
(74) *Attorney, Agent, or Firm* — Lerner David LLP

(57) ABSTRACT

In one embodiment, the present disclosure relates to fastener for use in a bone. The fastener includes a head and a shaft extending from the head. The shaft includes a threaded surface. When the shaft is subject to less than a predetermined torque, a distal portion of the shaft has a first configuration. When the shaft is subject to the predetermined torque, a distal portion of the shaft has a second configuration with the second configuration being different from the first configuration.

19 Claims, 11 Drawing Sheets

(56) References Cited

U.S. PATENT DOCUMENTS

| | | | | |
|---|---|---|---|---|
| 5,601,558 | A * | 2/1997 | Torrie | A61B 17/0401 606/232 |
| 5,720,753 | A * | 2/1998 | Sander | A61F 2/0811 606/104 |
| 5,733,307 | A | 3/1998 | Dinsdale | |
| 6,168,597 | B1 * | 1/2001 | Biedermann | A61B 17/86 606/310 |
| 6,206,883 | B1 | 3/2001 | Tunc | |
| 6,293,743 | B1 * | 9/2001 | Ernst | F16B 13/066 411/24 |
| 6,471,707 | B1 | 10/2002 | Miller et al. | |
| 6,575,976 | B2 * | 6/2003 | Grafton | A61F 2/0811 606/313 |
| 6,613,053 | B1 * | 9/2003 | Collins | A61B 17/7059 606/293 |
| 6,648,893 | B2 * | 11/2003 | Dudasik | A61B 17/686 606/327 |
| 6,668,688 | B2 * | 12/2003 | Zhao | A61B 17/8685 81/439 |
| 6,916,321 | B2 | 7/2005 | TenHuisen et al. | |
| 7,481,832 | B1 | 1/2009 | Meridew et al. | |
| 7,708,767 | B2 | 5/2010 | Contiliano et al. | |
| 8,075,588 | B2 | 12/2011 | Berberich et al. | |
| 8,211,156 | B2 * | 7/2012 | Andersen | A61B 17/8685 411/913 |
| 8,221,479 | B2 * | 7/2012 | Glazer | A61B 17/686 411/63 |
| 8,414,630 | B2 * | 4/2013 | Richelsoph | A61B 17/8625 606/328 |
| 8,480,342 | B2 | 7/2013 | Stiebitz et al. | |
| 8,574,273 | B2 | 11/2013 | Russell et al. | |
| 8,591,559 | B2 * | 11/2013 | Elahinia | A61B 17/8625 606/310 |
| 8,740,954 | B2 | 6/2014 | Ghobrial et al. | |
| 9,161,794 | B2 * | 10/2015 | Garvey | A61B 17/8615 |
| 9,211,153 | B2 | 12/2015 | Fisher et al. | |
| 9,265,542 | B2 | 2/2016 | Koay et al. | |
| 9,314,240 | B2 | 4/2016 | Paulk et al. | |
| 9,333,018 | B2 | 5/2016 | Russell et al. | |
| 9,393,006 | B2 | 7/2016 | Housman et al. | |
| 9,393,050 | B2 | 7/2016 | Karas et al. | |
| 9,492,159 | B2 | 11/2016 | Lunn et al. | |
| 9,526,547 | B2 | 12/2016 | Reed | |
| 9,707,059 | B2 | 7/2017 | Giorno | |
| 9,795,428 | B2 | 10/2017 | Levy et al. | |
| 9,848,927 | B2 | 12/2017 | Giorno | |
| 9,936,992 | B2 | 4/2018 | Russell et al. | |
| 9,987,063 | B2 | 6/2018 | Harris et al. | |
| 10,064,669 | B2 * | 9/2018 | Garvey | A61B 17/8685 |
| 10,064,707 | B2 | 9/2018 | Zadeh | |
| 10,265,107 | B2 | 4/2019 | Philippon | |
| 10,413,343 | B2 * | 9/2019 | Lindner | A61B 17/7035 |
| 10,449,032 | B2 | 10/2019 | Paulk et al. | |
| 10,507,041 | B2 | 12/2019 | Tsai et al. | |
| 10,531,904 | B2 | 1/2020 | Kolb | |
| 10,631,905 | B2 | 4/2020 | Asfora et al. | |
| 10,864,029 | B2 | 12/2020 | Redmond et al. | |
| 10,888,363 | B2 | 1/2021 | Greenhalgh et al. | |
| 11,000,326 | B1 | 5/2021 | Alon | |
| 11,045,238 | B2 | 6/2021 | Mehl et al. | |
| 11,076,901 | B2 | 8/2021 | Zastrozna | |
| 11,116,557 | B2 | 9/2021 | Zander et al. | |
| 11,147,603 | B2 | 10/2021 | Russell et al. | |
| 11,229,465 | B2 | 1/2022 | Tempco et al. | |
| 11,389,205 | B2 | 7/2022 | Corbin et al. | |
| 11,510,715 | B2 | 11/2022 | Reimels | |
| 11,857,224 | B2 * | 1/2024 | Wieser | A61B 17/7059 |
| 12,085,108 | B2 * | 9/2024 | Faghidi | E04B 1/74 |
| 12,226,129 | B2 * | 2/2025 | Sinnott | A61B 17/8605 |
| 12,390,258 | B2 * | 8/2025 | Sack | A61B 17/86 |
| 2002/0048496 | A1 | 4/2002 | Filipp | |
| 2002/0147454 | A1 * | 10/2002 | Neto | A61B 17/8685 606/313 |
| 2003/0065332 | A1 * | 4/2003 | TenHuisen | A61F 2/0811 606/909 |
| 2003/0125745 | A1 * | 7/2003 | Tseng | A61B 17/8605 606/907 |
| 2003/0138306 | A1 * | 7/2003 | Wallace | F16B 13/002 411/29 |
| 2004/0254581 | A1 * | 12/2004 | Leclair | A61B 17/8625 606/313 |
| 2005/0055027 | A1 * | 3/2005 | Yeung | A61B 17/0644 606/75 |
| 2006/0120822 | A1 * | 6/2006 | Kaye | F16B 13/124 411/30 |
| 2006/0127199 | A1 * | 6/2006 | Bappert | F16B 13/002 411/411 |
| 2008/0183220 | A1 * | 7/2008 | Glazer | A61B 17/686 606/301 |
| 2008/0208264 | A1 * | 8/2008 | Lazarof | A61C 8/0071 606/310 |
| 2008/0221624 | A1 * | 9/2008 | Gooch | A61B 17/70 606/302 |
| 2008/0234762 | A1 * | 9/2008 | Forstein | A61B 17/8635 606/301 |
| 2009/0192552 | A1 * | 7/2009 | Andersen | A61B 17/7032 606/302 |
| 2009/0281580 | A1 * | 11/2009 | Emannuel | A61B 17/8685 606/305 |
| 2010/0016905 | A1 * | 1/2010 | Greenhalgh | A61B 17/863 606/313 |
| 2010/0042164 | A1 * | 2/2010 | Lee | A61B 17/686 606/304 |
| 2010/0100135 | A1 * | 4/2010 | Phan | A61B 17/7064 606/301 |
| 2010/0217325 | A1 * | 8/2010 | Hochschuler | A61B 17/864 606/86 R |
| 2011/0257689 | A1 | 10/2011 | Fiechter et al. | |
| 2012/0083847 | A1 | 4/2012 | Huebner et al. | |
| 2014/0025125 | A1 * | 1/2014 | Sack | A61B 17/8625 606/232 |
| 2015/0359575 | A1 * | 12/2015 | Pech | A61B 17/866 606/291 |
| 2019/0350600 | A1 * | 11/2019 | Lehman, Jr. | A61B 17/1757 |
| 2019/0388131 | A1 * | 12/2019 | Mehl | A61B 17/1635 |
| 2020/0289179 | A1 * | 9/2020 | Zander | A61B 17/725 |
| 2020/0323574 | A1 * | 10/2020 | Picha | A61B 17/742 |
| 2021/0315622 | A1 | 10/2021 | Lacaze | |
| 2021/0401478 | A1 | 12/2021 | Russell et al. | |
| 2022/0104858 | A1 | 4/2022 | Ball | |
| 2023/0032203 | A1 * | 2/2023 | Maxwell | A61B 17/869 |

FOREIGN PATENT DOCUMENTS

| | | | |
|---|---|---|---|
| WO | 2021178484 | A1 | 9/2021 |
| WO | 2021181330 | A1 | 9/2021 |
| WO | 2021204951 | A1 | 10/2021 |
| WO | 2021252504 | A1 | 12/2021 |
| WO | 2022109338 | A1 | 5/2022 |

OTHER PUBLICATIONS

Ignatius, A.A. et al., "In Vitro Biocompatibility of Bioresorbable Polymers: Poly (L, DL-lactide) and Poly (L-lactide-co-glycolide)," Biomaterials, Jan. 1996, pp. 831-839, vol. 17, No. 8, Elsevier.

Laughlin, R.M. et al. "Resorbable plates for the Fixation of Mandibular Fractures: A Prospective Study," Journal of Oral and Maxillofacial Surgery, Jan. 2007, pp. 89-96, vol. 65.

Losken, H.W. et al., "Biodegradation of Inion Fast-Absorbing Biodegradable Plates and Screws," Journal of Craniofacial Surgery, May 2008, pp. 748-756, vol. 19.

Ricalde, P. et al., "Degradation Rate of Delta (Resorbable) Internal Fixation: Report of 2 Cases," Journal of Oral and Maxillofacial Surgery, Feb. 2004, pp. 250-255, vol. 62.

* cited by examiner

RESORBABLE SELF TAPPING SCREW

BACKGROUND OF THE DISCLOSURE

In surgical procedures necessitated by trauma to the face or cranial vault, plates may be used for repair or reconstruction. To secure such plates to bone, screws are commonly used. In some instances, the materials used for the plates and screws used are resorbable to avoid the need for removal. However, screws made of resorbable materials may provide inadequate fixation of the implanted plates and, even in cases where initial fixation is adequate, may weaken, break or dislodge over time. Resorbable screws and plates that have reduced anchorage and load bearing capacity may lead to post-surgical injury or infection and may require additional surgery to remedy. Another difficulty encountered with the use of existing screws in the cranio-maxillofacial region is the need to tap a pilot hole in the bone prior to screw installation. Pilot hole tapping increases the time and steps required for installation of resorbable screws and plates during surgery.

Accordingly, there is a need for resorbable screws with improved performance in repairs or reconstructions of bone damaged as a result of trauma.

BRIEF SUMMARY OF THE DISCLOSURE

In some aspects, the present disclosure generally relates to a fastener formed with recesses in its shaft that are shaped such that the fastener may respond to a particular amount of torque by breaking toward its distal end, changing the physical and performance characteristics of the fastener upon such breakage.

In a first aspect, the present disclosure relates to a fastener device. In a first example of a first embodiment, the fastener includes a head and a shaft. The shaft extends from the head and includes a threaded surface. The shaft includes a distal portion with a first configuration when the shaft is subject to less than a predetermined torque and a second configuration when the shaft is subject to the predetermined torque. The second configuration of the shaft is different from the first configuration of the shaft. The predetermined torque may be determined based on the design of the screw, where the design is tailored such that the predetermined torque may be expected to be reached upon penetration of materials through which the fastener is intended to be used.

In a second example, the first example of the first embodiment may be further defined by the outer surface of the distal portion having a first shape in the first configuration. In the second configuration, the outer surface of the distal portion may have a second shape different from the first shape. In a third example, the second example of the first embodiment may be further defined by the first shape having a first maximum cross-sectional dimension, and the second shape having a second maximum cross-section dimensions larger that the first maximum cross-sectional dimension. In a fourth example, the second example of the first embodiment may be further defined by when the distal portion has a first shape, a root surface of the shaft between crests of the thread and measured along a length of the shaft is parallel to a central longitudinal axis of the shaft. When the distal portion has the second shape, the root surface measured along the length of the shaft is non-parallel to the central longitudinal axis.

In a fifth example, the first example of the first embodiment may be further defined when the distal portion is in the first configuration, the distal portion is static with respect to a proximal portion of the shaft. When the distal portion is in the second configuration, at least a first part of the distal portion is moveable with respect to one or both of a second part of the distal portion and the proximal portion of the shaft. In a sixth example, the first example of the first embodiment may be further defined when the distal portion is in the first configuration, the distal portion has a first recess and a second recess. When the distal portion is in the second configuration, the distal portion has a single opening with a volume larger than the first recess combined with the second recess. In a seventh example, the first example of the first embodiment may be further defined when the distal portion is in the first configuration, a distal tip of the distal portion is a first distance from the head. When the distal portion is in the second configuration, the distal tip of the distal portion is a second distance from the head. The first distance being greater than the second distance.

In an eight example, the first embodiment may be further defined by the threaded surface of the shaft including a first thread and a second thread. In a ninth example, the eight example of the first embodiment may be further defined by the first and second threads being diametrically opposed to one another at a distal tip of the shaft. In a tenth example, the eight example of the first embodiment may be further defined by the first and second threads including interruptions at intervals along a length of the shaft. In an eleventh example, any one of the first through tenth examples of the first embodiment may include that the fastener is comprised of polymeric material.

In a twelfth example, the first example of the first embodiment may be further defined by the distal portion of the shaft including an internal bridge between two arms. The internal bridge being configured such that application of the predetermined torque to the shaft causes the internal bridge to break separating the two arms. In a thirteenth example, the first example of the first embodiment may be further defined by the internal bridge extending a length along the shaft equal to a length that the two arms extend along the shaft. In a fourteenth example, the first example of the first embodiment may be further defined by the internal bridge extending a length along the shaft less than a length that the two arms extend along the shaft. In a fifteenth example, the first example of the first embodiment may be further defined by the distal portion of the shaft including two recesses separating the two arms.

In a sixteenth example, the first example of the first fastener may be further defined in a system including the fastener and a plate. The plate is configured to receive the fastener such that a head of the fastener is flush with the plate surface when received in the plate. In a seventeenth example, the sixteenth example of the first embodiment may be further defined by the plate including a countersink configured to receive the fastener.

In an eighteenth example, the first example of the first embodiment may be further defined in a kit comprising the fastener and a plate. The plate is configured to receive the fastener. In a nineteenth example, the eighteenth example of the first embodiment may be further defined by the kit comprising a plurality of fasteners. In a twentieth example, the eighteenth example of the first embodiment may be further defined by the kit further comprising a plurality of plates.

In a first example of a second embodiment, a fastener includes a head, shaft, thread, and opposing recesses. The shaft extends from the head and has a convex surface. The thread is disposed on the convex surface. The opposing recesses are in the convex surface of the shaft and are separated from the head by a portion of the shaft. Over at least part of a length of the opposing recesses, the opposing recesses are separated by material of the shaft and the length of the opposing recesses is parallel to an elongate dimension of the shaft.

In a second example, the first example of the second embodiment may be further defined by the at least part of the length of the opposing recesses being coincident with a central portion of the shaft separating a base portion of the shaft adjacent to the head and a free-end portion of the shaft. The shaft having a pair of separated arms in the free-end portion, the pair of separated arms being deformable upon exertion of a predetermined torque on the shaft. In a third example, the first example of the second embodiment may be further defined by the material separating the opposing recesses is an internal bridge of material breakable upon exertion of a predetermined torque on the shaft.

In a fourth example, the first example of the second embodiment may be further defined by the thread being a first thread and the fastener further comprising a second thread. The first and second threads start at different locations at a base of the shaft abutting the head. In a fifth example, the fourth example of the second embodiment may be further defined by the first and second threads being diametrically opposed to one another at the base of the shaft abutting the head. In a sixth example, the fifth example of the second embodiment may be further defined by the first and second thread being diametrically opposed to one another along the convex surface of the shaft.

In a seventh embodiment, the first example of the second embodiment may be further defined by the material of the shaft being a central core of material that separates the opposing recesses entirely along their respective lengths. In an eight embodiment, the first example of second embodiment may be further defined by the material of the shaft being a central core of material that separates the opposing recesses along a portion of the length of the recesses that is less than the length of the respective recesses. In a ninth example, any of the first through eight examples of the second embodiment may be further defined by the central core of material being cylindrical in shape.

In a tenth example, the first example of the second embodiment may be further defined by the length of the opposing recesses being approximately 60% to 65% of a length of the shaft. In an eleventh example, the first example of the second embodiment may be further defined by each of the opposing recesses having a first end in between the head and a distal tip of the fastener and a second end at the distal tip. A size of the recess being smaller at the first end than the second end. In a twelfth example, the eleventh example of the second embodiment may be further defined by each of the opposing recesses flares outward from the first end toward the second end.

In a first example of a third embodiment, a fastener includes a head and a shaft. The shaft has a length from a base abutting the head to a tip. The shaft further includes a first thread and a second thread disposed thereon, the second thread being parallel to and offset from the first thread. Each of the first thread and the second thread includes an interruption at every half revolution of the thread such that a first axis passes through a first plurality of interruptions and a second axis passes through a second plurality of interruptions. The first axis and the second axis being on opposite sides of the shaft. Further, each interruption extends across a lateral width of the respective thread such that a lateral edge of the thread on a first side of the interruption is laterally offset from a lateral edge of the thread on a second side of the interruption. In a second example, the first example of the third embodiment may be further defined by the fastener being made of a polymeric material.

In a first example of a fourth embodiment, a fastener includes a head and a shaft. The shaft including a base surface with a radial projection thereon. The shaft extending from the head and including a distal portion. The distal portion having a first configuration when the shaft is subject to less than a predetermined torque and a second configuration when the shaft is subject to the predetermined torque. The second configuration being different from the first configuration.

In one aspect, the present disclosure relates to a method of implanting a prosthesis in a patient. In a first example of a first embodiment of such method, the method includes the following steps: placing a plate against a bone; positioning a fastener into a receiving surface of the plate, the fastener including a shaft; applying an initial torque to the fastener to at least penetrate a surface location of the bone with the fastener, and subsequent to applying the initial torque, and while maintaining the fastener at the surface location, applying a predetermined torque greater than the initial torque to transform the fastener from a first shape to a second shape.

In a second example, the first example of the first embodiment of such method may be further defined by the step of applying the predetermined torque to transform the fastener to the second shape includes a transformation of a shaft of the fastener from a first surface contour to a second surface contour different from the first surface contour. In a third example, the first example of the first embodiment of such method may be further defined by the step of applying the predetermined torque to transform the fastener to the second shape includes a transformation of a shaft of the fastener from having a cylindrical root surface to a flared-out root surface.

In a fourth example, the first example of the first embodiment of such method may be further defined by the step of the placing of the plate against the bone involves placing the plate against a facial bone. In a fifth example, the first example of the first embodiment of such method may be further defined by the step of spreading outward of the shaft occurs passively without the introduction of an additional structure into the fastener. In a sixth example, the first example of the first embodiment of such method may be further defined by during the rotating step, the distal portion engages with cancellous bone underneath the cortical layer when the torque in the shaft reaches the predetermined amount. In a seventh example, the first example of the first embodiment of such method may be further defined by the rotating step is performed without initially tapping a threaded hole into the bone receiving the fastener. In an eight example, the first example of the first embodiment of such method may be further defined by prior to the positioning step, a pilot hole is drilled into the bone. In a ninth example, the first example of the first embodiment of such method may be further defined by further including the step of absorbing the fastener into the bone after the rotating step.

In a tenth example, the first example of the first embodiment of such method may be further defined by when the predetermined amount of torque in the shaft is reached during the rotating step, a central bridge of material in the shaft that separates arms of the shaft breaks. In an eleventh example, the tenth example of the first embodiment of such method may be further defined by, the breaking of the internal bridge of the shaft causes the distal portion of the shaft to spread outward.

In one aspect, the present disclosure is a method of forming a fastener. In a first example of a second embodiment of such method, the method includes the following steps: supplying a volume of polymeric material into a mold of an injection molding system; curing the volume of polymeric material to form a solid polymeric material; removing the solid polymeric material from the mold, wherein the solid polymeric material is a fastener including a shaft with a first thread and a second thread thereon, the first and second threads having interruptions at half-revolution intervals along their lengths. In a second example, the first example of the second embodiment of such method may be further defined by the volume of polymeric material is supplied into a mold including a form inverse to the shaft with the first and second threads. The mold including an offset for lateral sides of the first and second threads at the interruptions.

BRIEF DESCRIPTION OF THE DRAWINGS

The features, aspects, and advantages of the present disclosure will become better understood with regard to the following description, appended claims, and accompanying drawings in which:

DETAILED DESCRIPTION

As used herein, the terms “about,” “generally,” and “substantially” are intended to mean that slight deviations from absolute are included within the scope of the term so modified. To aid the Patent Office and any readers of any patent issued on this application in interpreting the claims appended hereto, Applicant notes that it does not intend any of the appended claims or claim elements to invoke 35 U.S.C. § 112(f) unless the words “means for” or “step for” are explicitly used in the particular claim.

As used herein, the term “proximal,” when used in connection with a surgical tool or device, or components of a device, refers to the end of the device closer to the user of the device when the device is being used as intended. On the other hand, the term “distal,” when used in connection with a surgical tool or device, or components of a device, refers to the end of the device farther away from the user when the device is being used as intended.

In one aspect, the present disclosure relates to fasteners adapted for implantation in mammalian bone, and in particular in the craniomaxillofacial region. Such fasteners may be used to secure a bone plate in place as part of a surgery to repair or reconstruct bone damaged by trauma, or for cranial vault remodeling (reconstruction). In some examples, the fasteners may be screws. While the described embodiments reference craniomaxillofacial applications, it should be appreciated that the present application is not so limiting, and that the contemplated fasteners may be used in other regions of the body.

Figure 1:
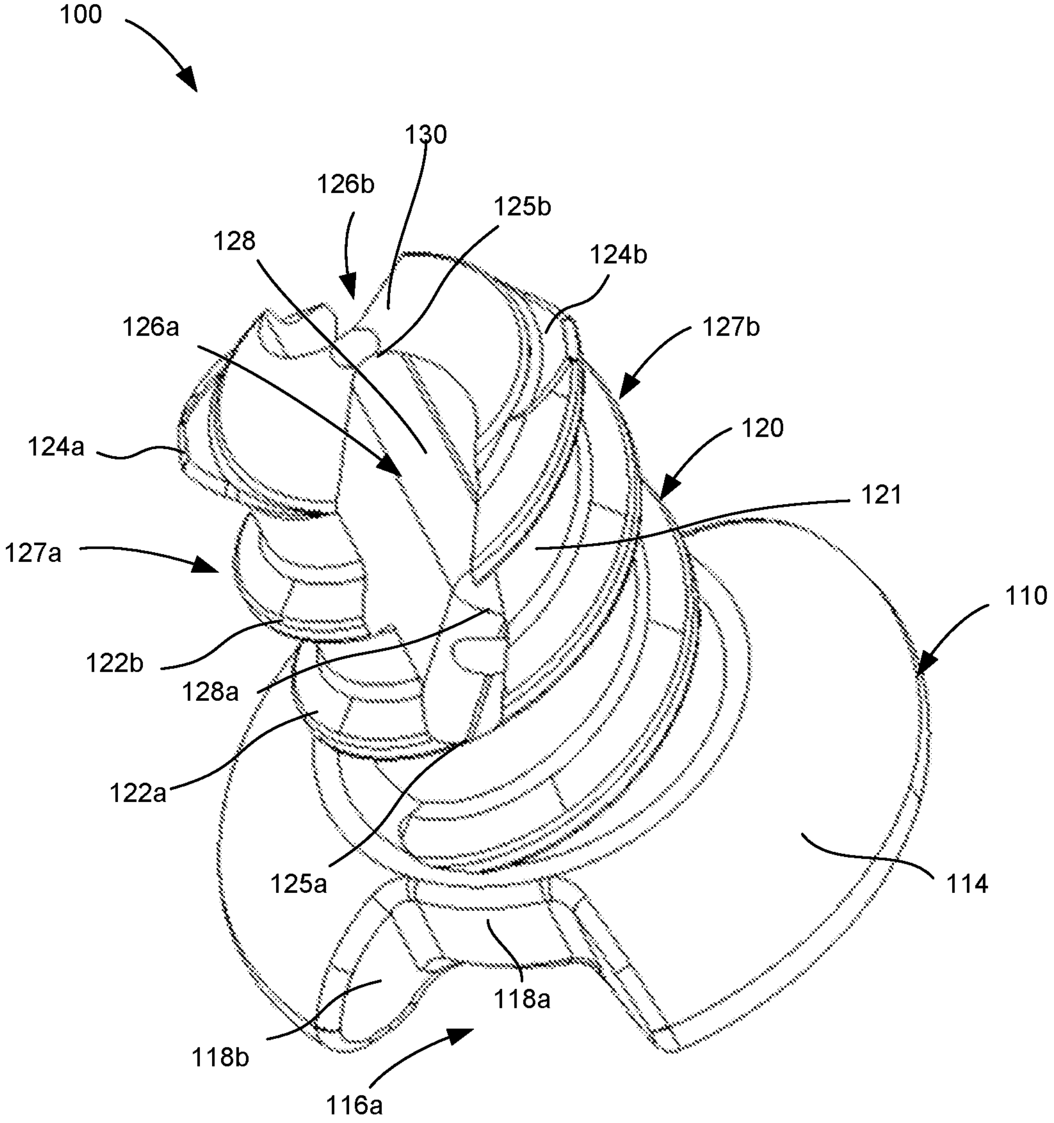
FIG. 1 is a perspective view of a fastener according to an embodiment of the present disclosure.
Figure 2:
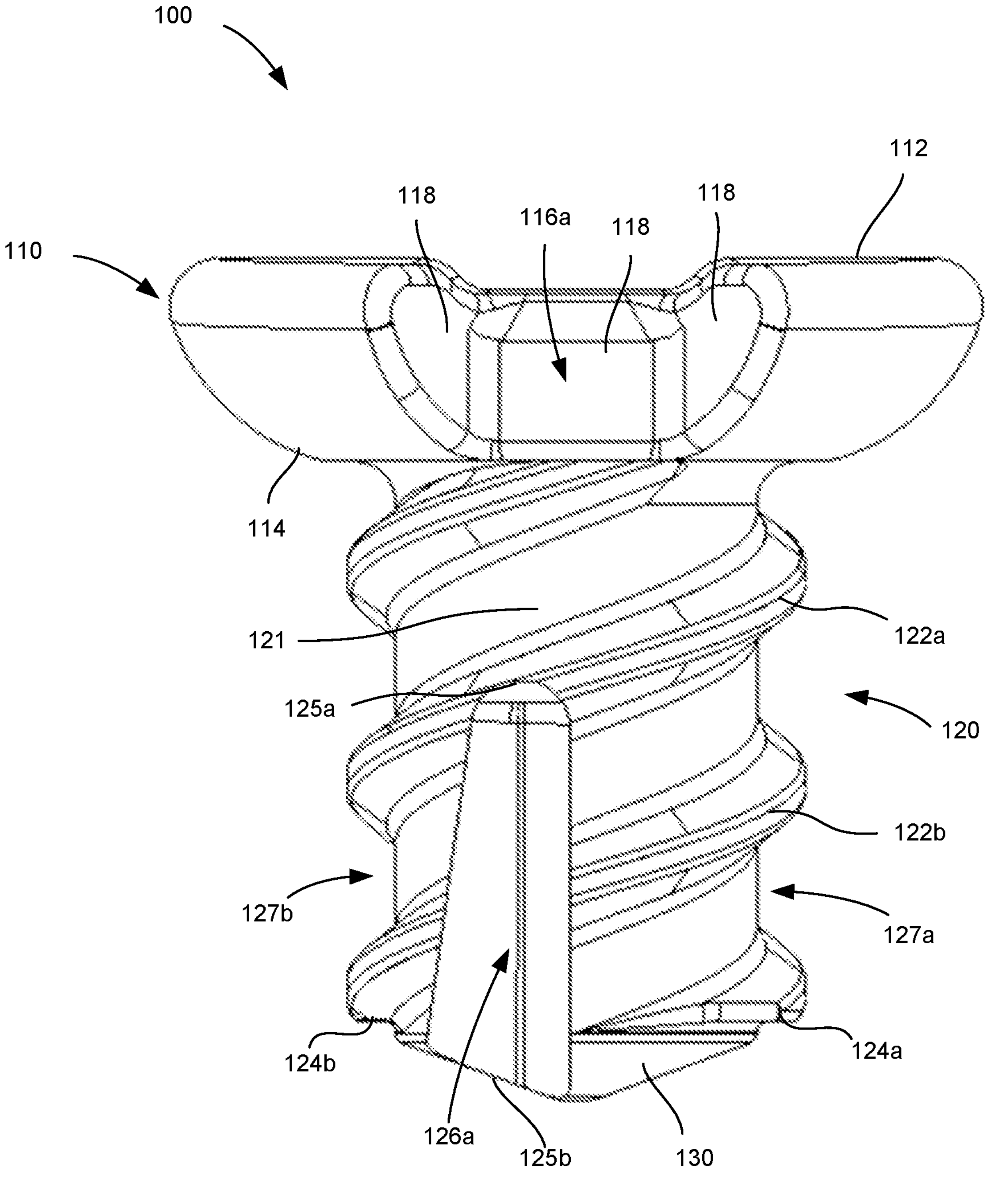
FIG. 2 is side view of the fastener of FIG. 1.
Figure 3:
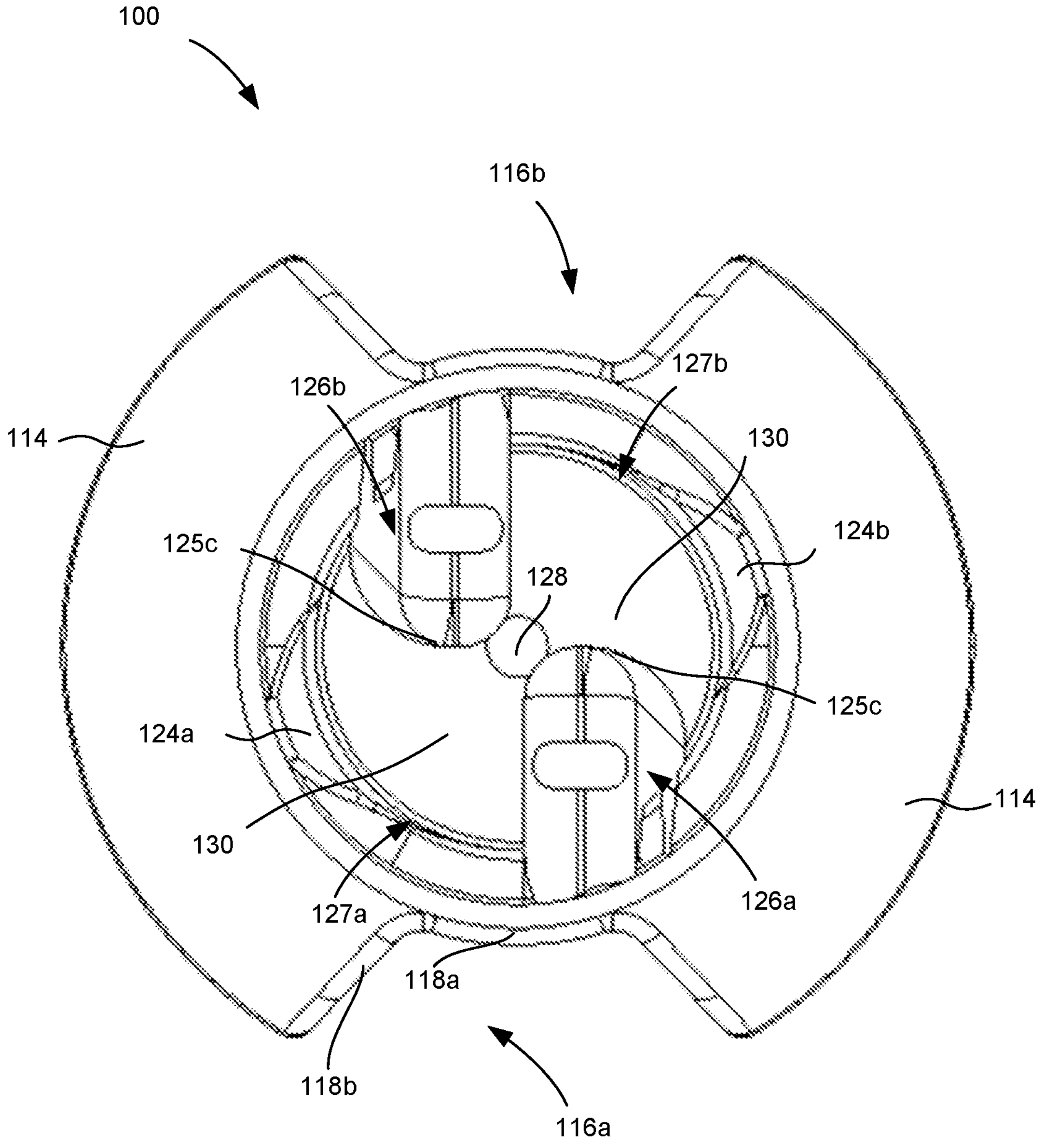
FIG. 3 is a bottom view of the fastener of FIG. 1.

FIGS. 1-3 illustrate a bone screw or fastener 100 according to one embodiment. The fastener 100 may be used for the fixation of plates to bones of the craniofacial and midfacial skeleton and includes a fastener head 110 and a fastener shaft 120. The fastener 100 may be formed from a polymeric compound. This polymeric compound may be, but is not limited to, any one of or a combination of poly lactic acid (PLA), poly L-lactide (PLLA), polyglycolide (PGA), poly D-lactide (PDLA), poly DL-lactic acid (PDLLA), wax, polyethylene (PE) and variations thereof, polyetheretherketone (PEEK), polyetherketone (PEK), acrylonitrile butadienestyrene (ABS), silicone, and cross-linked polymers. The fastener may also be formed from one or more of the aforementioned polymers, bioabsorbable glass, ceramics, and biologically active materials such as collagen/cell matrices. Composites of any one of or any combination of these materials may be made with any one of or any combination of bone cement, bone, soft tissue, and cellular matrices and tissue cells. In some examples, the fastener may be formed from a copolymer composition of poly L-lactide (PLLA), polyglycolide (PGA) and poly D-lactide (PDLA). In a subset of these examples, the aforementioned polymers are included in a ratio of 85:10:5. In some examples, the fastener may be formed from 100% PLA. In some examples, the fastener may be formed from 100% PDLLA. In other examples, the fastener may be a copolymer composition of PLLA and PGA in a ratio of 80:20 to 85:15. In still further examples, the fastener may be a copolymer composition of PLLA and PDLLA in a ratio of 70:30. The fastener 100 material may be resorbable into the bone. In some examples, a resorption rate of the fastener is such that the fastener is resorbed within approximately 8-13 months.

The head 110 includes a proximal surface 112 and a circumferential outer surface 114 that tapers from the proximal surface to the fastener shaft 120. The proximal surface 112 may be substantially planar and includes a tool recess (not shown) that defines a screw drive to receive a drive tool. The tool recess shape may be any shape compatible with screws for orthopedic applications. The screw may be a hex drive, square drive, or other known types. As best shown in FIG. 3, the head 110 includes opposing head recesses 116*a*, 116*b* that define a recess in the head such that a surface in the opening region has a similar profile to that of the shaft 120. The recesses 116*a*, 116*b* provide an additional interface for instrumentation used to engage the fastener. For example, some drive tools may include a screwdriver blade with flanges for engaging the recesses 116*a*, 116*b*, such engagement aiding in the retention of the fastener. In the depicted embodiment, the recesses 116*a*, 116*b* are diametrically opposed from one another on the circumferential outer surface 114 of the head 110. As best shown in FIG. 2, the recesses 116*a*, 116*b* are defined by a plurality of recess surfaces 118*a*, 118*b* configured in a somewhat U-shape direction towards a center of the head 110. The surfaces 118*a*, 118*b* include an outward-curving base surface 118*a* nearest to the center of the head 110, and a pair of planar side surfaces 118*b* extending outwards on an angle from respective ends of the base surface 118*a* to an outer circumference of the head 110. In other examples, the screw head may be absent any recesses.

The shaft 120 extends from the circumferential outer surface 114 of the head 110 to a distal end of the fastener 100 at a fastener tip 130. As shown in FIGS. 1-3, the shaft 120 has a convex base surface 121 and is cylindrical shape. The shaft 120 of the fastener 100 includes threads disposed thereon. While threads are referenced in the examples described throughout the disclosure, variations of the fastener may include radial projections on the shaft. As depicted, the threaded surface includes two threads, also referred to as a dual-start thread. The dual-start thread provides the fastener 100 with increased stability relative to a single-start thread during insertion into the bone. The threads are a first thread 122*a* and a second thread 122*b*. The first thread 122*a* extends from a first thread tip 124*a* to a base of head 110 while second thread 122*b* extends, in parallel to the first thread, from a second thread tip 124*b*, to the base of the head 110. As depicted, the thread tips 124*a*, 124*b* are diametrically opposed at the tip 130, and the threads 122*a*, 122*b* continue to be diametrically opposed along the base surface 121 of the shaft 120 to the head 110. In other examples, an offset between the respective threads may vary from the diametrically-opposed arrangement depicted in the Figures.

With continued reference to the shaft 120, the shaft further comprises a first shaft recess 126*a* and a second shaft recess 126*b*. As depicted, the recesses 126*a*, 126*b* are generally opposite one another and may have point symmetry as they extend from a first end 125*a* in a central region of the shaft 120 to a second end 125*b* proximate to the tip 130 at the distal end of the fastener 100. In this manner, a length of the recesses 126*a*, 126*b* is less than a length of the shaft 120. As best shown in FIG. 2, the recesses 126*a*, 126*b* extend into the central region of the shaft 120 exposing an interior of the shaft 120. Viewed from a side as shown in FIG. 2, the recesses 126*a*, 126*b* form a curved, semi-circular shape near the first end 125*a* in the central region of the shaft 120. As the recesses 126*a*, 126*b* extend distally towards the tip 130, the walls that define the shape of the recesses 126*a*, 126*b* gradually flare outward toward the tip 130 such that a dimension across each shaft recess gradually widens. As depicted, these walls are generally planar. The gradual widening of the recesses 126*a*, 126*b* is due to a first side of each recess 126*a*, 126*b* extending outward at an angle from the first end 125*a* to the second end 125*b*, and a second side of each recess 126*a*, 126*b* remaining parallel to a central longitudinal axis of the shaft 120. The recesses 126*a*, 126*b* may also be defined with first side and second sides in other orientations relative to one another. The opening at the second end 125*b* of the recesses 126*a*, 126*b* is defined at least in part by a portion of the distal tip 130. Because the recesses 126*a*, 126*b* extend over a significant portion of the shaft length, such recesses interrupt the threads 122*a*, 122*b* disposed along the base surface 121.

Turning to a shape of the shaft recesses 126*a*, 126*b* from a central axis of the shaft to an outer perimeter, as shown from below in FIG. 3, the recesses 126*a*, 126*b* are defined in part by a curved wall 126*c* proximate a central longitudinal axis of the shaft, the curved wall 126*c* being offset from the central longitudinal axis such that the shaft opening does not encompass any part of the longitudinal axis. Moving radially from an interior of the shaft toward shaft base surface 121, the curved wall 126*c* transitions into opposing planar walls. In some examples, a depth of each shaft recess is slightly less than a radius of the shaft, the difference between the depth and the radius being a distance from the center of the shaft to an outside of a central core of material at the center. The central core is described in greater detail below.

A remainder of the shaft 120 surrounding the recesses 126*a*, 126*b* defines a first arm 127*a* and a second arm 127*b*, as shown in FIGS. 1-3. The arms 127*a*, 127*b* extend distally from a first end along a length of the shaft 120 at a similar axial location as the first end 125*a* of recesses 126*a*, 126*b* to the tip 130. The arms 127*a*, 127*b* include a portion of the threads 122*a*, 122*b* along their respective outer surfaces. A length of the arms 127*a*, 127*b* measured along an elongate direction of the shaft 120 may be any amount in a range from approximately 45% to 75% of a length of the shaft. In certain specific examples, the length of the arms 127*a*, 127*b* may be in a range from 60% to 65% of the shaft 120 length. In many examples, the opposing arms 127*a*, 127*b* may have the same length. In some examples, a length of one arm may vary to an extent with respect to the other.

The arms 127*a*, 127*b* are connected to one another by a central core of material 128. The central core 128 has an elongate dimension that extends along the central longitudinal axis of the shaft 120 and separates the shaft recesses 126*a*, 126*b* from one another. The central core 128 may be integral with the arms 127*a*, 127*b* to define a single monolithic structure. The central core 128 extends distally from a predetermined point 128*a* along the central axis of the shaft 120 to the tip 130 at the distal end of the fastener 100. As depicted, the central core 128 is cylindrical in shape. A diameter of the central core 128 may be from approximately 8% to approximately 20% of a diameter of the base of the shaft 120 as defined by the base surface 121. In certain specific examples, the diameter may be in a range from 13% to 14% of a diameter of the shaft 120 as measured at the base surface 121. In other examples, a ratio of a diameter of the central core relative to a diameter of the shaft may be outside of the above identified ranges. It should also be appreciated that a particular ratio of central core to shaft diameter may be a function of the materials used. In fastener 100, central core 128 has a length commensurate with a length of the arms 127*a*, 127*b*. In other examples, and as described in greater detail below, a length of the central core 128 may not be commensurate with a length of the arms 127*a*, 127*b* as shown in FIGS. 1-3, i.e., the length of the central core may be shorter than that of the arms. The structure of the fastener 100 is such that it is self-tapping and thus does not require the preparation of a threaded hole to receive the fastener during its implantation into bone.

In some examples, a diameter measured at the base surface 121 of the fastener 100 may be any amount in a range from 1.0 mm to 5.0 mm. In certain subsets of these examples, the diameter may be 2.0 mm, 2.2 mm or 2.4 mm. In some examples, a length of the fastener 100 may be any amount in a range from 3.0 mm to 12 mm. In certain subsets of these examples, the length may be 4.0 mm or 6.0 mm. In some examples, the length may be inclusive of the head and the shaft. In other examples, the length may be based on the shaft alone. In one example of fastener 100 shown in FIGS. 1-3, if the diameter is 2.2 mm, then the length may be 4.0 mm. Further, while the above dimensions are illustrative, it should be appreciated that the concepts of the present disclosure are not limited to fasteners having the particular dimensions identified.

Figure 4:
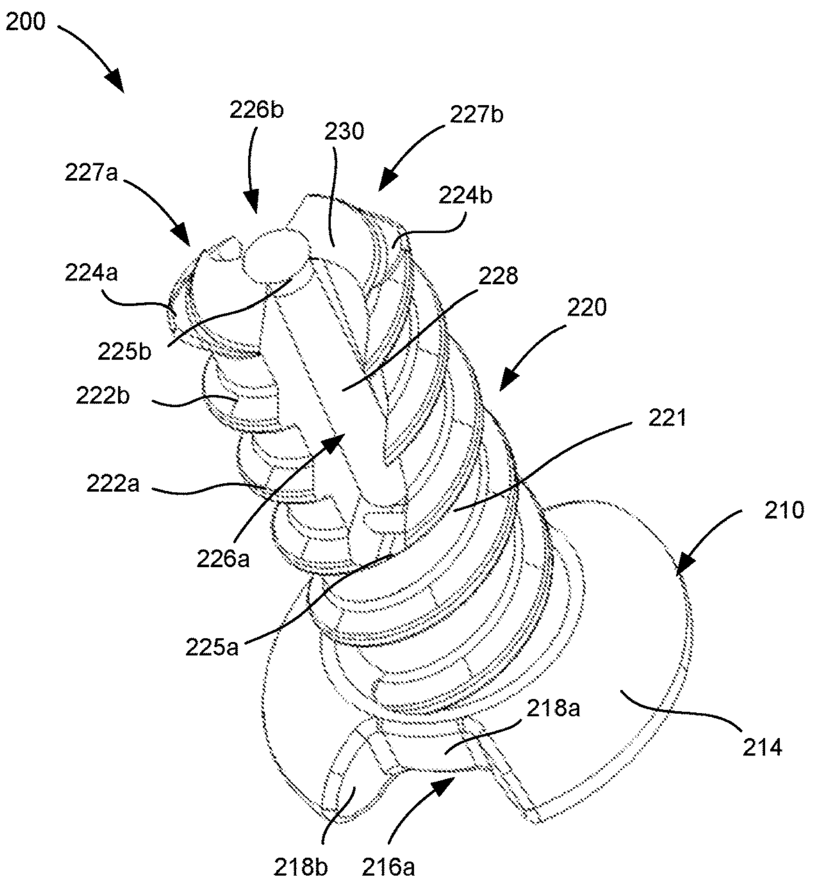
FIG. 4 is a perspective view of a fastener according to another embodiment of the present disclosure.
Figure 5:
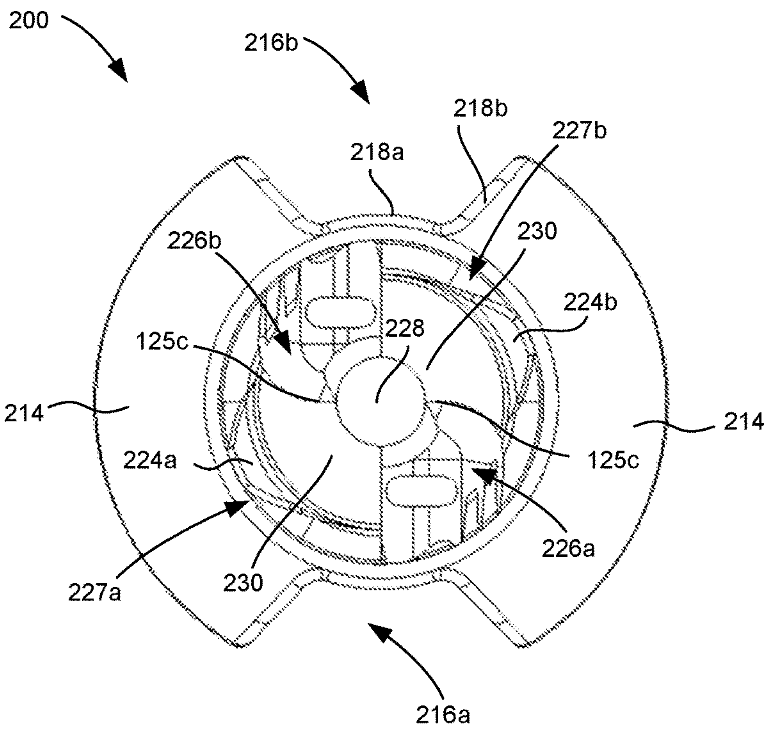
FIG. 5 is a bottom view of the fastener of FIG. 4.

FIGS. 4-5 illustrate a fastener 200 according to another embodiment of the present disclosure. For ease of review, like elements will be accorded like reference numerals to that of fastener 100, but within the 200-series of numerals. The fastener 200 includes a fastener head 210, a fastener shaft 220, and a fastener tip 230. The shaft 220 may have an elongate dimension along its central longitudinal axis longer than the shaft 120. In one example of fastener 200 shown in FIGS. 4-5, if the diameter is 2.2 mm, then the length may be 6 mm. Further, a first and second shaft recess 226*a*, 226*b*, a first and second arm 227*a*, 227*b*, and a central core 228 may each have elongate dimensions along the central longitudinal axis proportionally longer relative to that of recesses 126*a*, 126*b*, arms 127*a*, 127*b*, and central core 128, respectively. The central core 228 may have a greater diameter relative to the diameter of the shaft 220 when compared to that of the relationship between the core 128 and the shaft 120. The recesses 226*a*, 226*b*, therefore, extend a shorter distance from the central core 228 to the outer surface of the shaft 220 compared to that of the recesses 126*a*, 126 of shaft 120. The fastener 200 may be varied in the ways described above for fastener 100.

Figure 6:
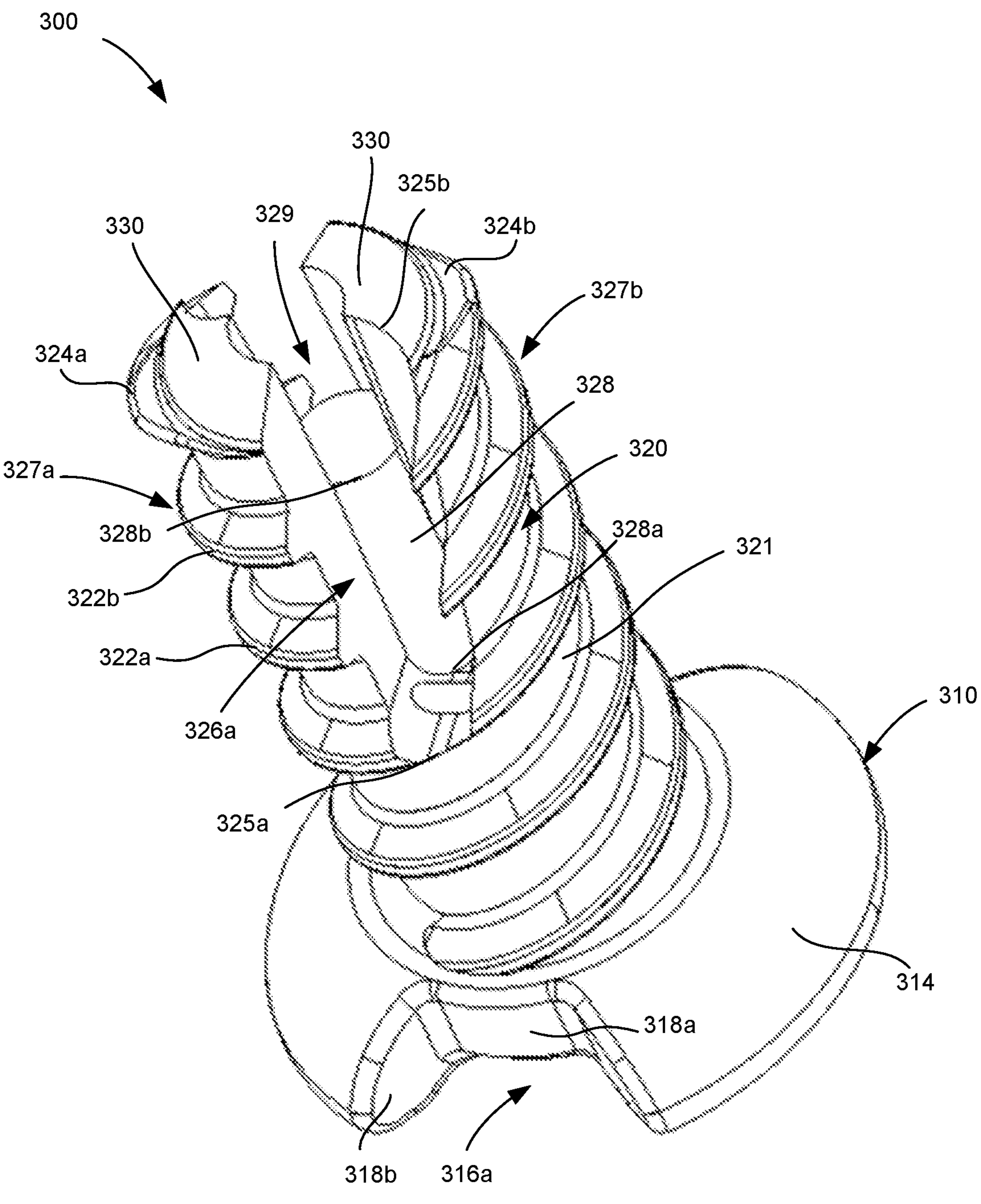
FIG. 6 is a perspective view of a fastener according to another embodiment of the present disclosure.
Figure 7:
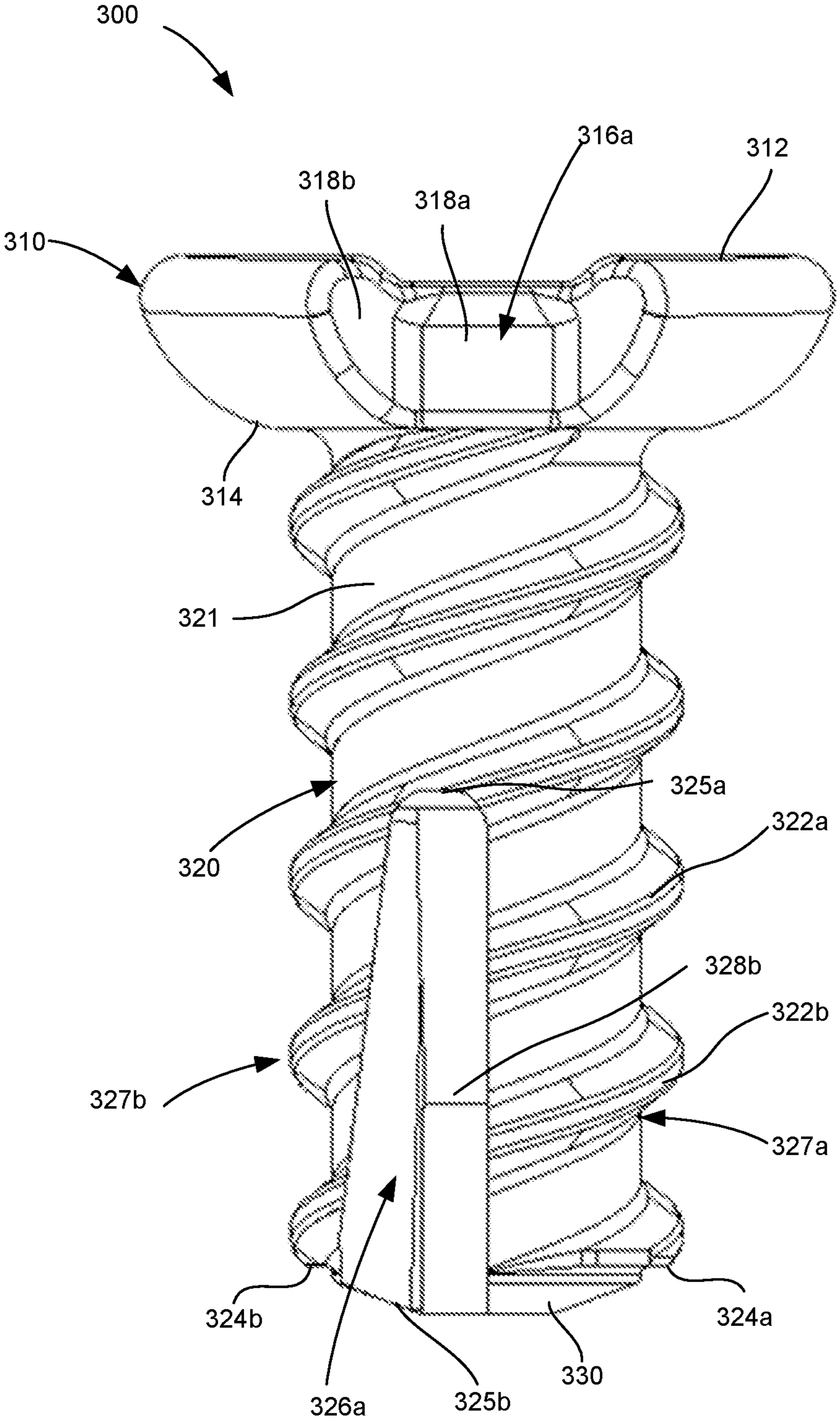
FIG. 7 is a side view of the fastener of FIG. 6.
Figure 8:
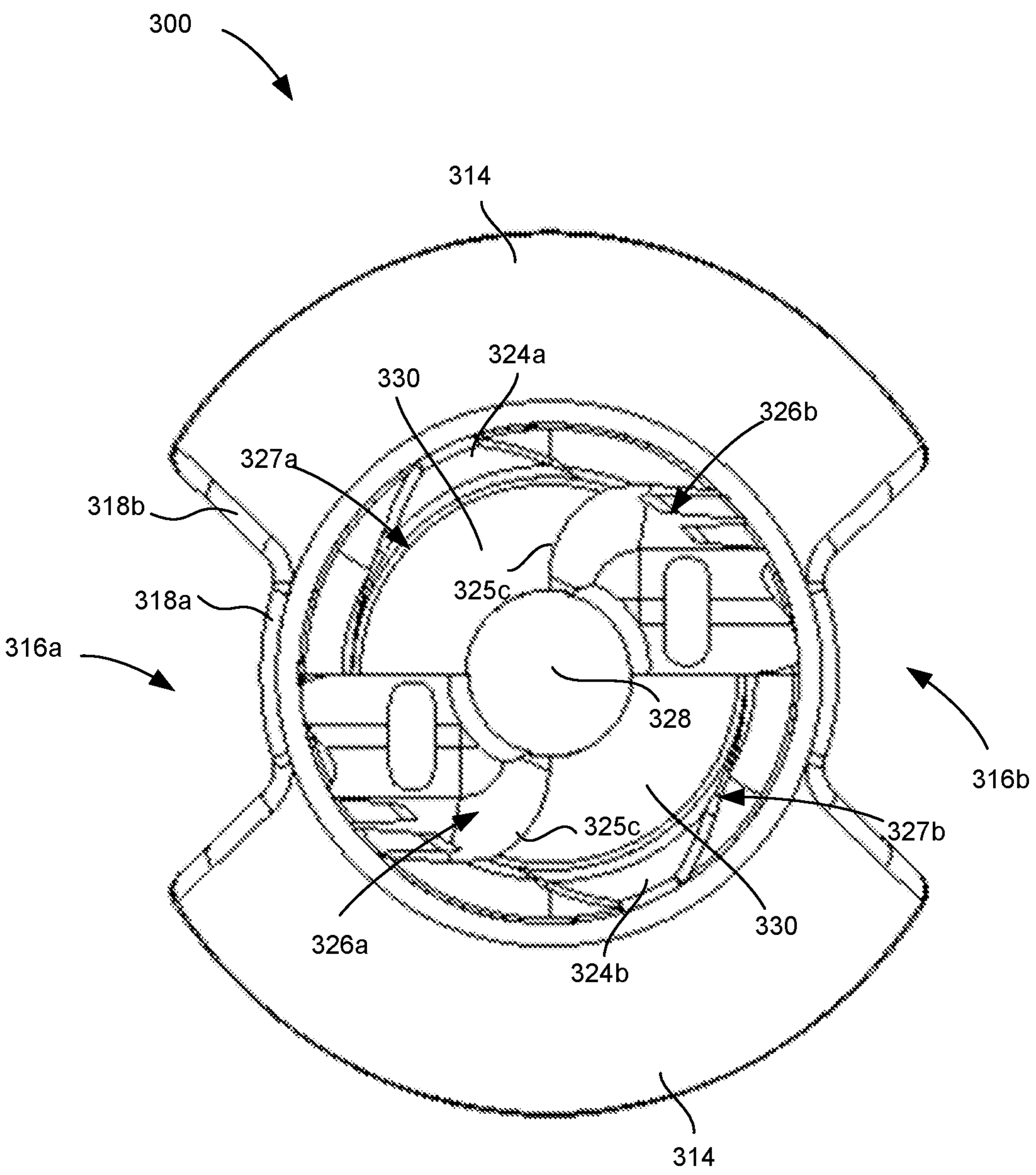
FIG. 8 is a bottom view of the fastener of FIG. 6.

FIGS. 6-8 illustrate a fastener 300 according to another embodiment of the present disclosure. For ease of review, like elements will be accorded like reference numerals to that of the fastener 100, but within the 300-series of numerals. The fastener 300 includes a fastener head 310, a fastener shaft 320, and a fastener tip 330. The central core 328 of fastener 300 extends along a longitudinal axis of the shaft 320 from a predetermined point 328*a* in a central region of the shaft to a distal end of the central core 328*b* in a central region of the shaft. The distal end 328*b* is remote from the tip 330 such that the shaft 320 includes an opening 329 from distal end 328*b* and the tip 330 and between arms 327*a*, 327*b*. As with fasteners 100, 200, central core 328 separates arms 327*a*, 327*b* over part of a length of the respective arms. In fastener 300 as depicted, central core 328 may have a length of any amount ranging from approximately 50% to approximately 60% of a length of arms 327*a*, 327*b*. In certain specific examples, the length of the central core may be 56%, 57% or 58% of a length of the arms. In other examples, the length may be below or above the 50-60% range. Compliance of the shaft may be a function of a length of the central core in that the shorter the length of the central core relative to a length of the arms, the greater the compliance.

Figure 9:
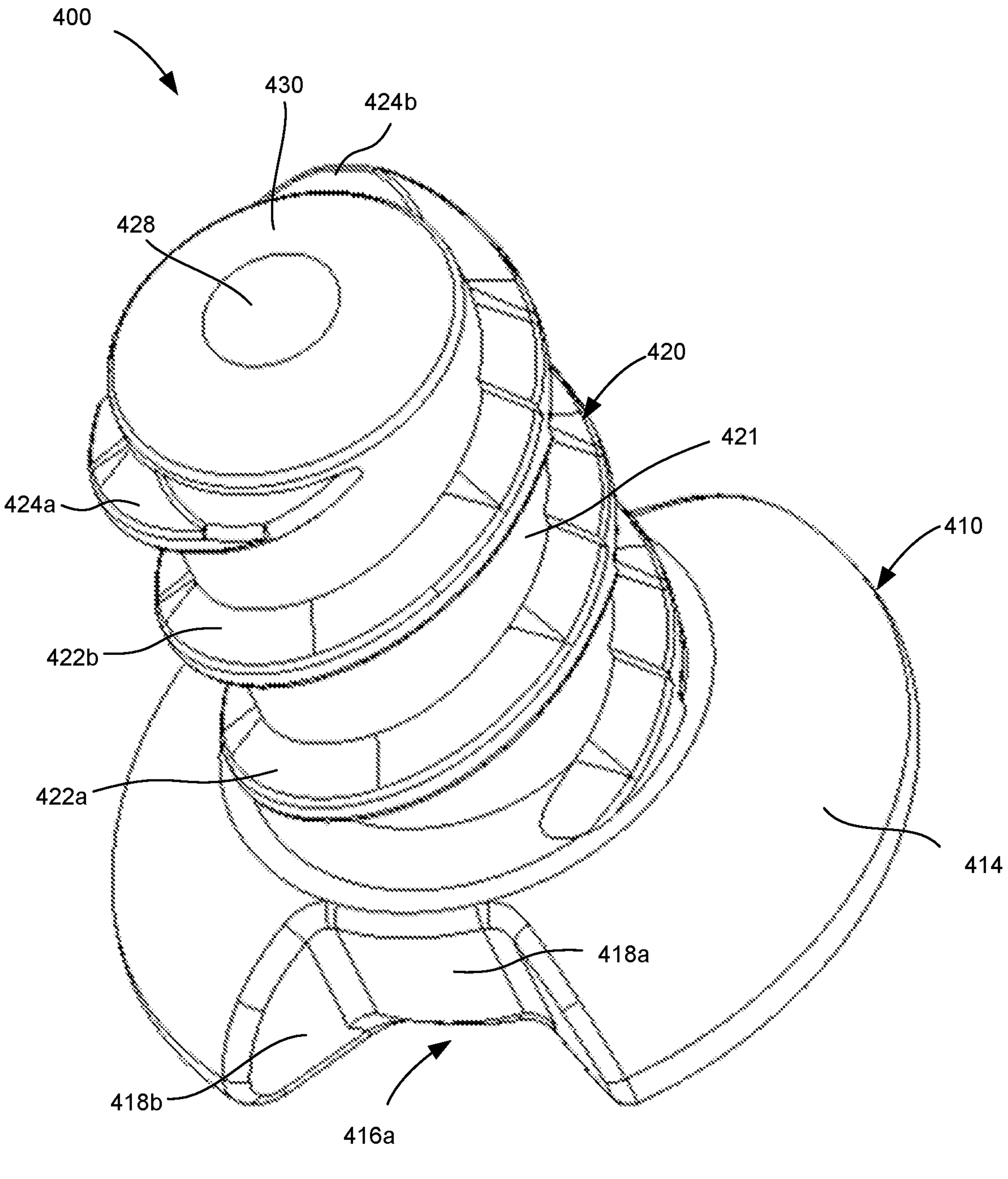
FIG. 9 is a perspective view of a fastener according to another embodiment of the present disclosure.
Figure 10:
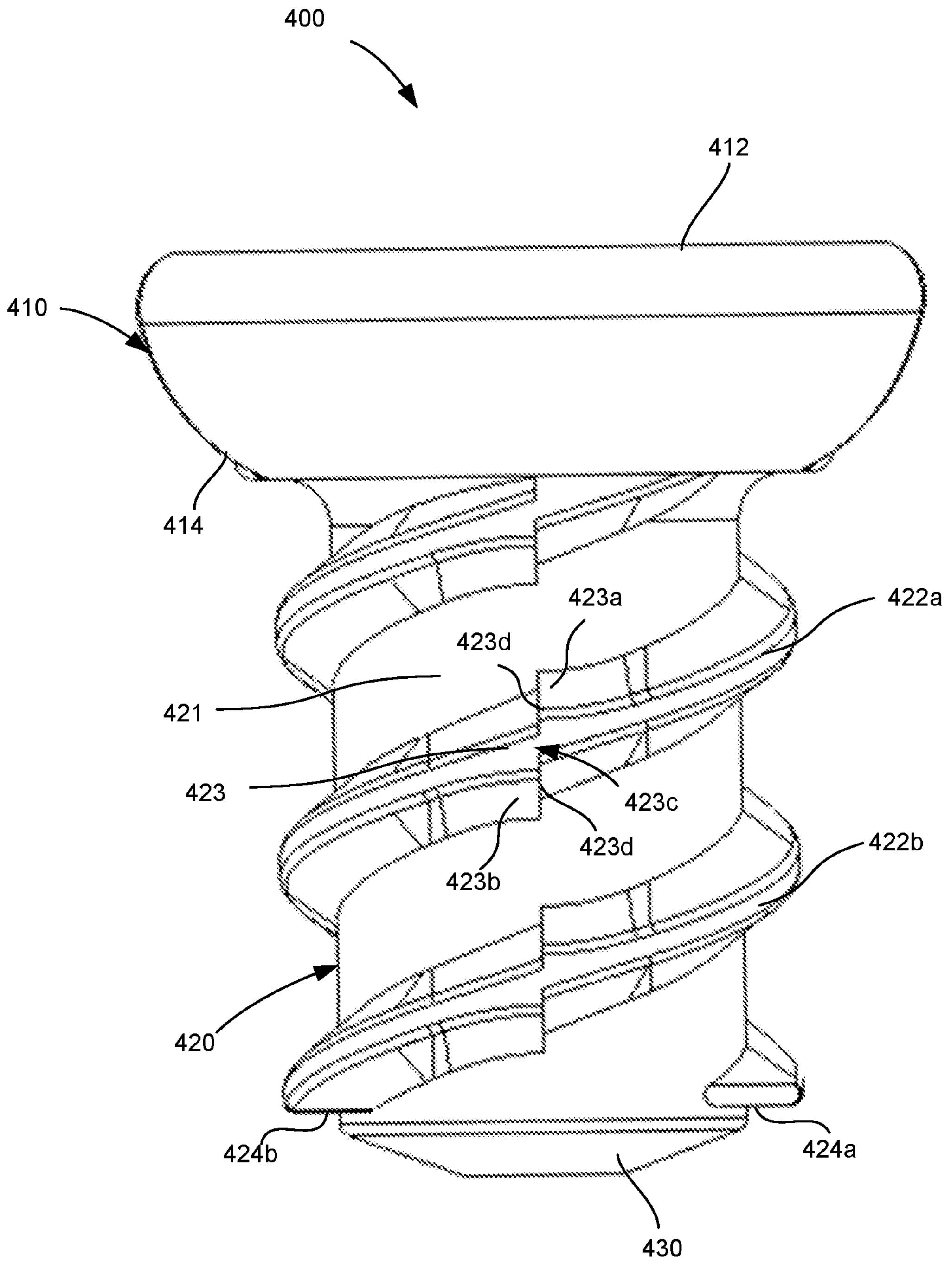
FIG. 10 is a side view of the fastener of FIG. 9.
Figure 11:
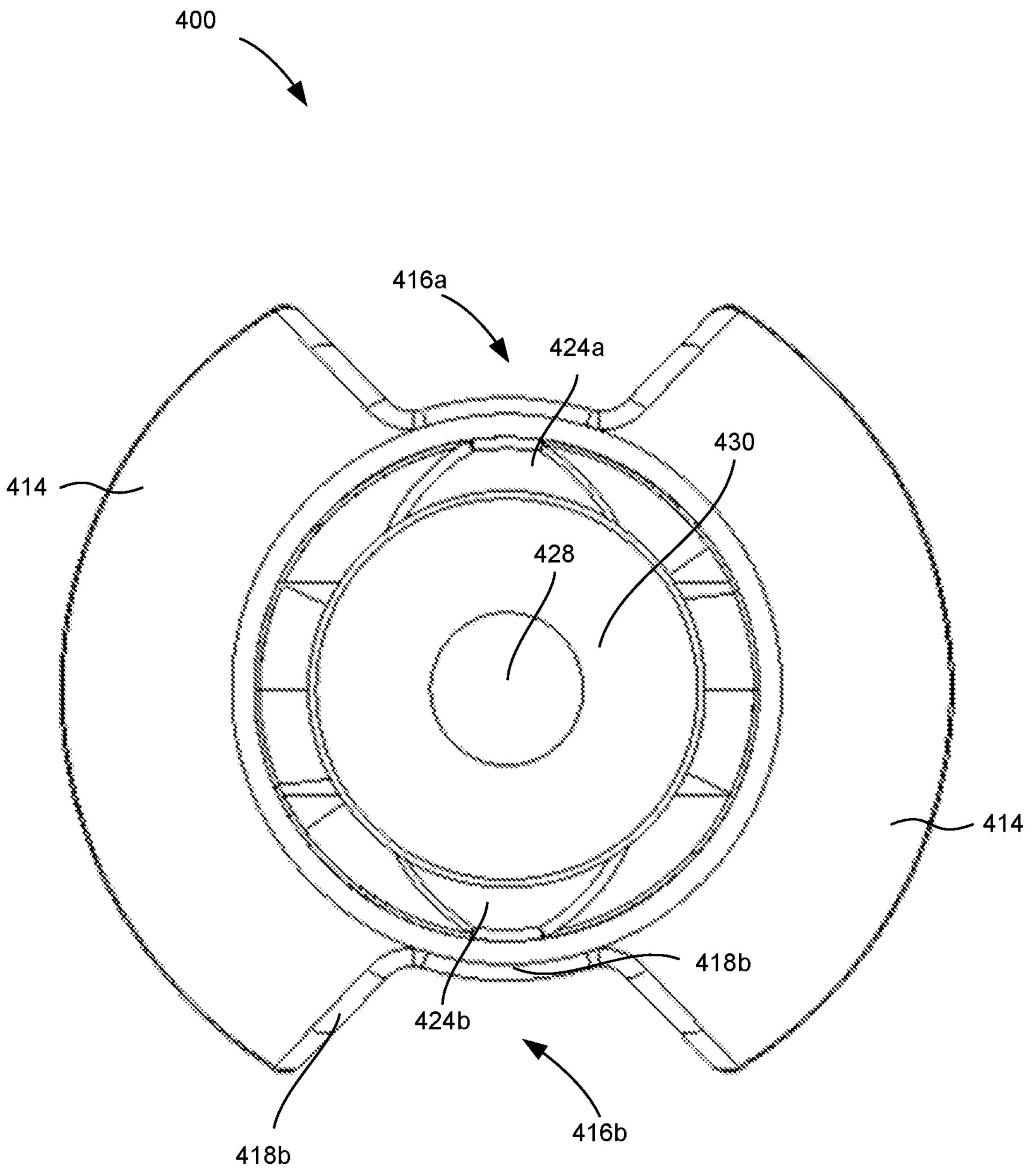
FIG. 11 is a bottom view of the fastener of FIG. 9.

FIGS. 9-11 illustrate a fastener 400 according to yet another embodiment of the disclosure. For ease of review, like elements will be accorded like reference numerals to that of fastener 100, but within the 400-series of numerals. Fastener 400 includes a plurality of interruptions 423 along first and second threads 422*a*, 422*b*. One representative interruption of fastener 400 is indicated by 423 in FIG. 10. The interruption 423 separates first and second thread portions 423*a*, 423*b* that are offset from each other along a length direction of the shaft 420. In this manner, the interruption 423 includes an edge 423*d* that extends across a width of the thread and along an axis parallel to a central longitudinal axis of the shaft 420. The thread portions 423*a* and 423*b* are offset from each other such that lateral edges of the thread define a step at the edge 423*d*. A first plurality of interruptions 423 may be disposed such that each respective edge 423*d* is aligned along an axis parallel to that of the center longitudinal axis of the shaft 420. A second plurality of interruptions on the threads may be diametrically opposed to first plurality of interruptions 423 along the outer surface of the shaft 420. Although not shown, the fasteners 100, 200, and 300 may, in some examples, include a shaft with threads having a plurality of interruptions as described above.

The fastener may be varied in many ways. For example, the fastener may include a triple start thread that extends from the tip along the outer surface of the shaft to the base of the head. The triple start thread may be disposed upon the outer surface of the shaft in a similar manner to that of the threads of fastener 100. Further, in some examples, the fastener may include four or more threads. It should be appreciated that in other embodiments, the fastener may include a single thread along a length of the shaft, although such arrangement may result in reduced stability during initial insertion of the fastener through a plate and into a recipient bone.

Further, in some examples, the central core may have a rectangular or conical cross-sectional shape. The cross-sectional dimension of the central core may taper or expand as it extends distally from its base in an interior of the shaft towards the tip. The central core may also change from one shape to another as it extends from the predetermined point along the inner shaft towards the tip. Further, while shaft openings are depicted in a particular manner for fasteners 100, 200, 300, it should be appreciated that the surface contours and overall wall shape defining the shaft opening cross-sectional shape and its side profile may be varied from that shown in FIGS. 1-8. Further, a relationship between opposing shaft openings may also vary from that shown in terms of a location of the respective openings on opposite sides of a plane separating the two openings. For example, while fastener 100 has point symmetry in a plane passing through a length and center of the shaft, dividing a cross-section of the shaft into equal parts, the openings may be varied to shift the openings from such symmetry. Moreover, in some variations, one opening may be larger than the other.

In another aspect, the present disclosure relates to a kit with components for cranio-maxillofacial repair or reconstruction. In one embodiment, a kit includes a bone screw or fastener as contemplated in the present disclosure. The kit of this embodiment may include any number of fasteners and two or more fasteners may have different sizes. Moreover, the kit of this embodiment may have fasteners of two or more types. In another embodiment, a kit includes a bone screw or fastener as contemplated in the present disclosure and a bone plate. The kit of this embodiment may include any number of fasteners and any number of plates. Two or more fasteners may have different sizes and two or more plates may have different sizes. A head of each of the fasteners are configured to engage with an opening of each plate. The fasteners and plates of the kit may be resorbable into the bone. In any of the above embodiments, a kit may further include an instruction manual with an explanation of details relating to the contents of the kit including instructions for use of the contents.

In another aspect, the present disclosure relates to a method of implanting a fastener into a bone. The fastener may be used to secure a bone plate to the bone. In some embodiments, the fastener may be implanted into a craniomaxillofacial bone. It should be understood that the following operations do not have to be performed in the exact order described below. Instead, various steps may be handled in a different order or simultaneously. Steps may also be omitted or added unless otherwise stated herein.

In some embodiments, the fastener 100 is used for the fixation of plates to bones of the craniofacial and midfacial skeleton. It should be appreciated that fasteners 100, 200, and 300 are interchangeable for the purposes of the described method but reference is made to fastener 100 specifically solely for the sake of brevity. Additional details of plates that may be used for these methods include those described in U.S. Pat. Nos. 9,987,063, and 6,206,883, the entire disclosures of which are incorporated by reference herein.

Figure 12:
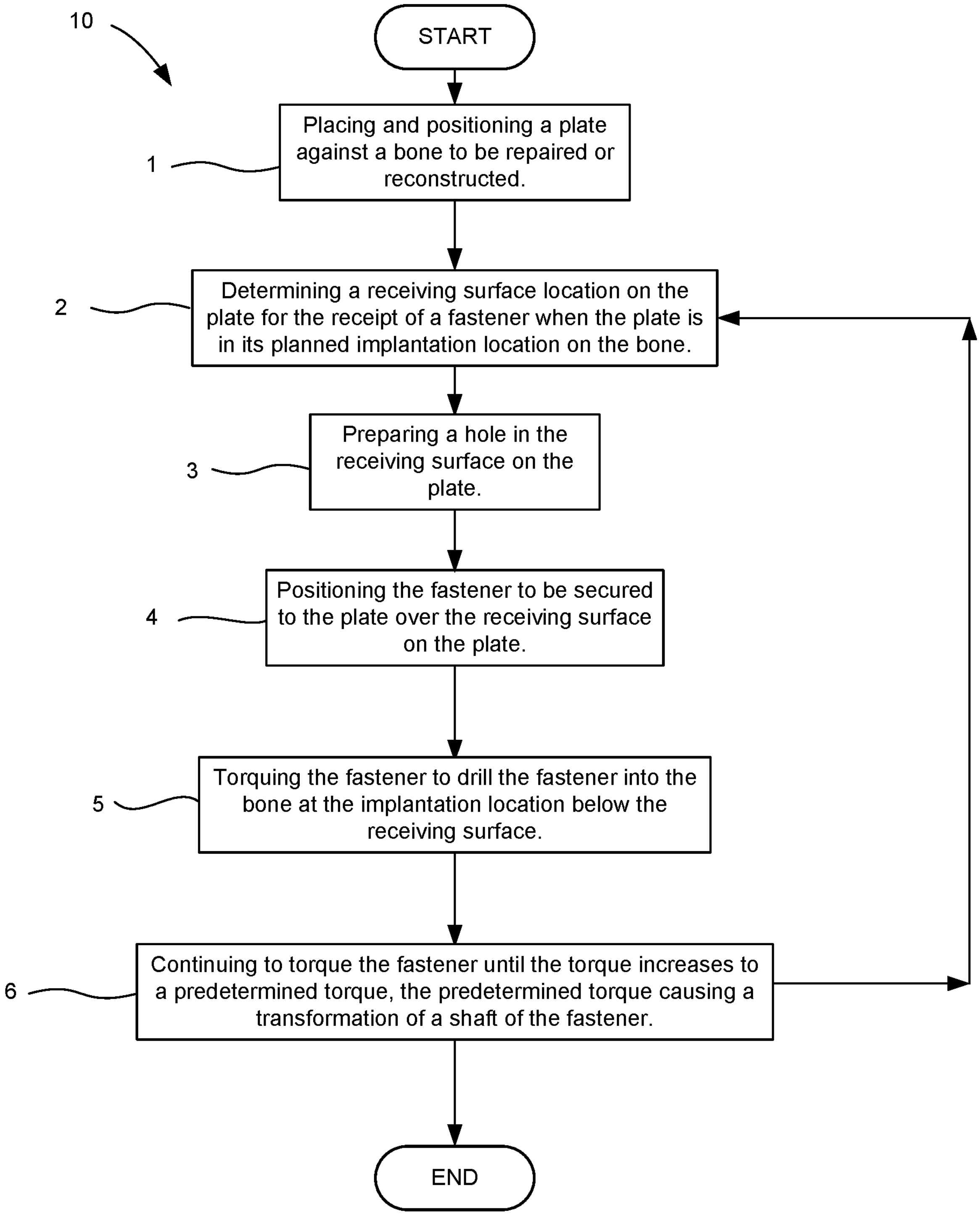
FIG. 12 is a flow chart showing a method of using the fastener of with a plate and a bone according to an embodiment of the present disclosure.

In one non-limiting embodiment, steps of which are shown in FIG. 12, a method 10 of implanting a fastener into a bone begins at step 1 where a plate is positioned on a bone to be repaired, such as the maxilla. In step 2, using the plate as a reference, fastener placement locations on the plate are determined based on the implantation location of the plate on the bone. In step 3, a hole or holes may be prepared through the plate at locations on the plate identified for receiving a fastener 100. If the plate includes countersinks or other identifiable recesses, a hole may be prepared through the plate at the countersink located at the desired fastener 100 implantation location. This step may be repeated for all fasteners 100 to be implanted through respective implantation locations on the plate. As part of step 3 or as an additional step following step 3, pilot holes may be prepared in the bone at the implantation locations. Because the fastener 100 is self-tapping, there is no need to prepare a threaded hole in the bone in preparation for receipt of the fastener 100. Alternatively, where the materials used to form the fastener have characteristics sufficient to allow the fastener to penetrate through bone without a pilot hole, the method 10 may proceed from step 2 directly to step 4. In step 4, the fastener 100 is positioned over an installation location on the plate. When plates with countersinks are used, the fastener 100 is placed over a countersink that corresponds to a planned implantation location.

In step 5, a torque is applied to the fastener 100 to drill the fastener into the bone. As the fastener 100 is drilled into the bone, the torque in the shaft of the fastener 100 may increase with the drilling action. In step 6, it is expected that the torque in the shaft of the fastener 100 will reach a predetermined level, and upon reaching that level, the opposing arms 127*a*, 127*b* will deform. The deformation of the opposing arms 127*a*, 127*b* may in some cases cause the central core 128 of the fastener to break or fracture along its length. The predetermined level of torque may be based on the design characteristics of the screw itself, such as length, diameter, and material(s), among other characteristics. For example, the screw shaft openings and central core may be shaped and sized such that the arms deform or the central core reaches failure at torques necessary to pass through hard tissue, such as a maxillary cortical bone structure. If the central core 128 breaks, a split is formed toward the distal portion of the fastener, thereby fully separating the opposing arms 127*a*, 127*b*. As the drilling continues with the altered structure of the fastener 100, the split arms 127*a*, 127*b* may transform by moving laterally in an outward direction from a central longitudinal axis of the shaft 120 or in other directions relative to the central longitudinal axis. As the split arms bend and spread, the fastener 100 may push into the receiving material, which may be a soft tissue such as cancellous bone when the implantation is into a maxilla. The pushing action creates a press fit within the receiving material. The dual-configuration characteristic of the fastener, in other words, a fastener with a pre- and post-central core breakage configuration, provides stronger structural fixation and reinforcement to the bone than fasteners without such transformative characteristics. After anchorage of the fastener, the method may continue from step 2 for a second fastener, and for any subsequent fasteners until all plates or other prostheses are secured in place.

It should be appreciated that the fastener 400 may also be used according to method 10 as described above. While the method steps employed may be the same, certain performance characteristics of the fastener may vary due to the differences between fastener 400 and fasteners 100, 200, 300.

In yet another aspect, the present disclosure relates to a method of manufacturing a fastener. In some embodiments, the fastener is formed using an additive layer manufacturing ("ALM"), i.e., 3D printing, process. In some examples, ALM processes are powder-bed based and involve one or more of selective laser sintering (SLS), selective laser melting (SLM), electron beam melting (EBM), fused deposition modeling (FDM), or another appropriate 3D printing technology known to those skilled in the art. Non-metallic materials may be used in the ALM process and include, but are not limited to, implantable plastics. These may be any one of or a combination of PLLA, PGA, PDLA, wax, PE and variations thereof, PEEK, PEK, ABS, silicone, cross-linked polymers, other polymers mentioned elsewhere in the present disclosure, bioabsorbable glass, ceramics, and biological active materials such as collagen/cell matrices. Composites of any one or any combination of these materials may be made as a combination with any one or any combination of bone cement, bone, soft tissue, and cellular matrices and tissue cells. Other methods of manufacture may also be used, such as milling. It should be appreciated that specific dimensions and surface contours of the various subparts of the fastener may be varied through the selective use of a particular manufacturing technique.

In some embodiments, a fastener is formed through a single, continuous ALM process. Put another way, the fastener is formed layer by layer in a single step. This approach may be employed to form any one of fasteners 100, 200, 300, and 400, for example. The geometry and other properties of the fastener is programmed into software associated with the ALM system, e.g., computer and machine, and then used to produce its elements in a single pass.

In other embodiments, a fastener may be formed using injection molding techniques. Standard injection molding techniques may be used to form the fastener. In one example, injection molding to form the fastener may be performed in the manner described in U.S. Pat. Nos. 6,206,883 and 5,192,326, the entire disclosures of which are incorporated by reference herein. Fasteners with interruptions as contemplated by the present disclosure are one example of fasteners that may be formed using injection molding techniques. An injection molding system with molds shaped to form thread interruptions, such as those shown in FIG. 10 including interruption 423, reduce the risk that the fastener will be damaged when it is de-molded and otherwise removed from the system.

Although the disclosure herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

The invention claimed is:

1. A fastener comprising:

a head;

a shaft extending from the head, the shaft having a convex surface;

a thread disposed on the convex surface; and opposing planar recesses in the convex surface of the shaft, the opposing planar recesses being separated from the head by a portion of the shaft, and the opposing planar recesses extending to a distal tip of the fastener, wherein over at least part of a length of the opposing planar recesses, the opposing planar recesses are separated by an integral core extending along a central axis of the shaft, the core being monolithic with at least a portion of the shaft, and wherein the length of the opposing planar recesses is parallel to the central axis of the shaft, and wherein the at least part of the length of the opposing planar recesses is coincident with a central portion of the shaft separating a base portion of the shaft adjacent to the head and a free-end portion of the shaft, the shaft having a pair of separated arms in the free-end portion, the pair of separated arms being deformable upon exertion of a predetermined torque on the shaft.

2. The fastener of claim 1, wherein the core separating the opposing planar recesses is an internal bridge of material breakable upon exertion of a predetermined torque on the shaft.

3. The fastener of claim 1, wherein the thread is a first thread and the fastener further comprises a second thread, the first and second threads starting at different locations at a base of the shaft abutting the head.

4. The fastener of claim 1, wherein the core of the shaft is a central core of material that separates the opposing planar recesses along a portion of the length of the recesses that is less than the length of the respective recesses.

5. The fastener of claim 1, wherein each of the opposing planar recesses has a first end in between the head and the distal tip of the fastener and a second end at the distal tip, a size of each of the opposing planar recesses at the second end being wider than a size of each of the opposing planar recesses at the first end.

6. The fastener of claim 5, wherein each of the opposing planar recesses flares outward from the first end toward the second end.

7. A fastener comprising:

a head; and a shaft having a length from a base abutting the head to a tip, the shaft including a continuous first thread and a continuous second thread disposed thereon, the second thread being parallel to and offset from the first thread, wherein each of the first thread and the second thread includes an interruption at every half revolution of the thread such that a first axis passes through a first plurality of interruptions and a second axis passes through a second plurality of interruptions, the first axis and the second axis being on opposite sides of the shaft, and wherein each interruption extends across a lateral width of the respective thread such that a lateral edge of the thread on a first side of each interruption is offset from a lateral edge of the thread on a second side of each interruption.

8. The fastener of claim 7, wherein for a first interruption of the first plurality of interruptions, a first lateral edge on a first side of the first interruption and abutting the first interruption is closer to the head than the first lateral edge on a second side of the first interruption and abutting the first interruption.

9. The fastener of claim 8, wherein for the first interruption, a second lateral edge on the second side of the first interruption opposite from the first lateral edge and abutting the first interruption is closer to the tip than the second lateral edge on the first side of the first interruption and abutting the first interruption.

10. The fastener of claim 7, wherein each interruption of the first plurality of interruptions and the second plurality of interruptions is defined in part by a step in the flank of one of the first thread and the second thread.

11. The fastener of claim 7, wherein at least one interruption from among the first plurality of interruptions or the second plurality of interruptions separates first and second thread portions that are offset from each other along a length direction of the shaft.

12. The fastener of claim 7, wherein the first axis and the second axis are parallel to a central longitudinal axis extending through the shaft.

13. The fastener of claim 7, wherein the fastener is made of a polymeric material.

14. The fastener of claim 7, wherein the shaft further comprises a third thread disposed thereon.

15. The fastener of claim 7, wherein the fastener is self-tapping.

16. The fastener of claim 7, wherein a crest of one of the first thread and the second thread extends across at least one interruption of the first plurality of interruptions and the second plurality of interruptions.

17. The fastener of claim 16, wherein a surface of the crest is the same distance from a central longitudinal axis of the shaft on a first side of the at least one interruption, on a second side of the at least one interruption opposite the first side, and at the at least one interruption.

18. The fastener of claim 7, wherein the first thread and the second thread extend along the entire length of the shaft from the base to the tip.

19. A system comprising:

the fastener of claim 7; and a bone plate comprising at least one opening configured to receive the fastener.

* * * * *